US007732211B2

(12) United States Patent
Kelsey et al.

(10) Patent No.: US 7,732,211 B2
(45) Date of Patent: Jun. 8, 2010

(54) METHOD AND APPARATUS FOR SCREENING OF POLYCONDENSATION CATALYSTS

(75) Inventors: Donald Ross Kelsey, Fulshear, TX (US); Kathleen Suzanne Kiibler, Katy, TX (US)

(73) Assignee: Avantium International B.V., Amsterdam (NL)

( * ) Notice: Subject to any disclaimer, the term of this patent is extended or adjusted under 35 U.S.C. 154(b) by 1006 days.

(21) Appl. No.: 10/398,949

(22) PCT Filed: Oct. 12, 2001

(86) PCT No.: PCT/NL01/00752

§ 371 (c)(1),
(2), (4) Date: Jul. 25, 2003

(87) PCT Pub. No.: WO02/31483

PCT Pub. Date: Apr. 18, 2002

(65) Prior Publication Data

US 2004/0014225 A1    Jan. 22, 2004

Related U.S. Application Data

(60) Provisional application No. 60/240,327, filed on Oct. 13, 2000.

(51) Int. Cl.
*G01N 31/10*     (2006.01)
*G01N 33/44*     (2006.01)
*F26B 7/00*      (2006.01)
*F26B 19/00*     (2006.01)

(52) U.S. Cl. .................. 436/37; 34/92; 34/406; 34/408; 34/412; 422/99; 422/102; 422/104; 422/129; 422/130; 422/131; 436/85; 436/159

(58) Field of Classification Search ............ 422/129, 422/130–131, 99, 102, 104; 436/37, 85, 436/159, 183; 34/92, 406, 408, 549, 559, 34/412; 159/28.1, 28.6, 29
See application file for complete search history.

(56) References Cited

U.S. PATENT DOCUMENTS

| | | | | | |
|---|---|---|---|---|---|
| 2,345,548 | A | * | 3/1944 | Flosdorf et al. | ............ 34/299 |
| 2,360,108 | A | * | 10/1944 | Christie | ............ 34/255 |
| 2,496,054 | A | * | 1/1950 | Hoyler | ............ 159/28.1 |
| 2,735,804 | A | * | 2/1956 | Lynch | ............ 208/127 |
| 2,803,888 | A | * | 8/1957 | Cerletti | ............ 34/62 |
| 3,072,362 | A | * | 1/1963 | Allen | ............ 406/188 |
| 3,145,562 | A | * | 8/1964 | Hamilton et al. | ............ 73/76 |
| 3,161,710 | A | * | 12/1964 | Turner | ............ 264/216 |

(Continued)

OTHER PUBLICATIONS

Stevenson, R. W., Journal of Polymer Science 1969, 7, 395-407.*

(Continued)

*Primary Examiner*—Arlen Soderquist
(74) *Attorney, Agent, or Firm*—Hoffmann & Baron, LLP

(57) ABSTRACT

The present invention relates to a method for screening of polycondensation catalysts, wherein at least two polycondensation catalysis reactions are performed simultaneously under substantially equivalent conditions in at least two reaction cells which are present in one and the same room, using a sample comprising material to be polycondensated and a catalyst to be screened, and wherein the performances of the catalysts are analyzed.

The present invention further relates to an apparatus suitable for performing the method.

16 Claims, 1 Drawing Sheet

U.S. PATENT DOCUMENTS

| | | | |
|---|---|---|---|
| 3,192,184 A * | 6/1965 | Brill et al. | 526/71 |
| 3,258,313 A * | 6/1966 | Griffiths | 422/106 |
| 3,346,541 A * | 10/1967 | Davies et al. | 528/279 |
| 3,907,754 A * | 9/1975 | Tershansy et al. | 528/277 |
| 3,977,935 A * | 8/1976 | Kowarski | 159/23 |
| 4,003,713 A * | 1/1977 | Bowser | 422/101 |
| 4,141,373 A * | 2/1979 | Kartanson et al. | 75/403 |
| 4,612,363 A * | 9/1986 | Sasaki et al. | 528/274 |
| 4,670,404 A * | 6/1987 | Swift et al. | 436/147 |
| 5,053,454 A * | 10/1991 | Judd | 525/54.11 |
| 5,293,697 A * | 3/1994 | Kawakami | 34/92 |
| 5,464,590 A * | 11/1995 | Yount et al. | 422/131 |
| 5,472,672 A * | 12/1995 | Brennan | 422/131 |
| 5,516,490 A * | 5/1996 | Sanadi | 422/101 |
| 5,604,130 A * | 2/1997 | Warner et al. | 435/286.7 |
| 5,792,430 A * | 8/1998 | Hamper | 422/131 |
| 6,043,335 A | 3/2000 | Marianucci et al. | |
| 6,054,100 A * | 4/2000 | Stanchfield et al. | 422/102 |
| 6,063,633 A * | 5/2000 | Willson, III | 436/37 |
| 6,572,828 B1 * | 6/2003 | Potyrailo et al. | 506/39 |
| 2003/0216253 A1 * | 11/2003 | Wiegner et al. | 502/208 |

OTHER PUBLICATIONS

Hanak, J. J., Journal of Materials Science 1970, 5, 964-971.*
Wolf, K.-H. et al, Angewandte Makromolekulare Chemie 1978, 68, 23-37.*
Rafler, G. et al, Angewandte Makromolekulare Chemie 1983, 116, 109-124.*
Rafler, G. et al, Acta Polymerica 1988, 39, 315-320.*
Rybnikar, F. et al, Macromolecular Chemistry and Physics 1994, 195, 81-104.*
Kubota, Y. et al, Catalysis Today 1996, 31, 27-43.*
Chung, T.-S. et al, Journal of Physical Chemistry B 1999, 103, 108-114.*
Cheng, S.-X. et al, Chemical Engineering Science 1999, 54, 663-674.*
Cheng, S.-X. et al, Journal of Physical Chemistry B 1999, 103, 4923-4932.*
Cheng, S.-X. et al, Journal of Polymer Science, Part B: Polymer Physics 1999, 37, 3084-3096.*
Rybnikar, F. et al, Journal of Polymer Science, Part B: Polymer Physics 1999, 37, 3520-3531.*
Chung, T.-S. et al, Journal of Polymer Science, Part A: Polymer Chemistry 2000, 38, 1257-1269.*
Hashimoto, T. et al, SPIE 2000, 3941, 36-44.*
Schumann, H. D., Mitteilungen, Industrie-Forschungszentrum Chemieanlagen 1969, 9, 108-112.*
Tomita, K., Polymer 1976, 17, 221-224.*
Rafler, G. et al, Journal of Macromolecular Science, Chemistry 1985, A22, 1413-1427.*
Gamlen, G. A. et al, Thermochimica Acta 1986, 106, 105-113.*
Kushimoto, T. et al, Catalysis Today 1993, 16, 571-578.*
Lu, T.-S. et al, Journal of Polymer Science, Part A: Polymer Chemistry 1995, 33, 2841-2850.*
Ueda, M. et al, Polymer 1997, 38, 3369-3372.*
Moon, S. I. et al, Journal of Polymer Science, Part A: Polymer Chemistry 2000, 38, 1673-1679.*
Korshak, V. V. et al, Khimicheskaya Nauka i Promyshlennost 1959, 4, 546-547.*
Zimmermann, H. et al, Abhandl. Deut. Akad. Wiss. Berlin, Kl. Chem., Geol. Biol. 1965, 19-27.*
Campbell, G. A. et al, Journal of Applied Polymer Science 1970, 14, 1025-1035.*
Pell, T. M., Jr. et al, Journal of Polymer Science, Polymer Physics Edition 1973, 11, 1671-1682.*
Cai, F. et al, Shiyou Huagong 1990, 19, 11-16.*
Kobayashi, F. et al, Kogyo Kagaku Zashi 1971, 74, 1244-1247.*
Moulijn J.A. et al: "General Aspects of Catalyst Testing" Catalysts Today, Amsterdam, NL. vol. 1, No. 11, Nov. 27, 1991, pp. 1-12.
Jensen J.V. et al: "A deactivation reactor for catalyst screening and evaluation" Proceedings International Gongress on Catalysis, vol. 2, 1977, pp. 796-805.
Heinemann H: "Catalyst Performance Testing" Catalysts Today, Amsterdam, NL, vol. 2, No. 22, Dec. 12, 1994, pp. 281-293.

* cited by examiner

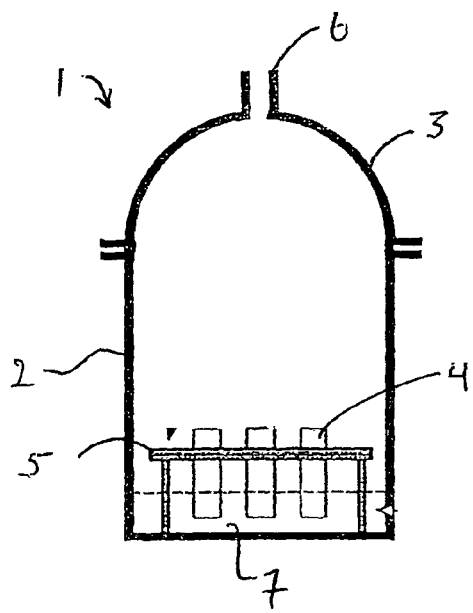
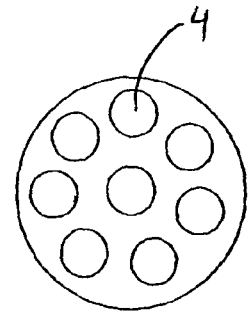
Fig. 1
Fig. 2
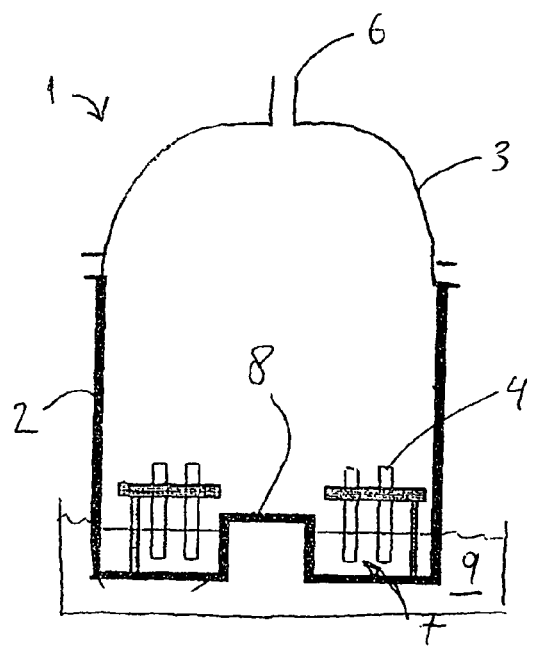
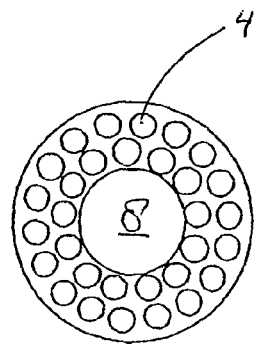
Fig. 3
Fig. 4

METHOD AND APPARATUS FOR SCREENING OF POLYCONDENSATION CATALYSTS

CROSS-REFERENCE TO RELATED APPLICATIONS

This application is the national stage filing under 35 U.S.C.§371 of PCT/NL01/00752, filed Oct. 12, 2001, which claims priority to U.S. Provisional Application No. 60/240,327, filed Oct. 13, 2000.

BACKGROUND OF THE INVENTION

The present invention relates to a method for screening of polycondensation catalysts, wherein at least two polycondensation catalysis reactions are performed simultaneously under substantially equivalent conditions in at least two reaction cells, using a sample comprising material to be polycondensated and a catalyst to be screened, and wherein the performances of the catalysts are analyzed.

Polycondensation catalysts vary in their ability to speed up the reactions for polymerizing e.g. polyesters, particularly for those prepared from diols and diacids (or diesters). Polycondensation reactions and catalysts are known in the field. Examples of polycondensation catalysts are e.g. $Ti(OBu)_4$, $Ti(O-iPr)_4$, $Sb(OBu)_3$, $Al(O-sBu)_3$, $Ge(OEt)_4$, etc.

In practice polycondensation catalyst are screened using classical laboratory equipment, e.g. glass or metal reaction vessel, stirrer, etc.

A problem of the known methods for screening polycondensation catalysts is that laboratory screening takes about a day per polymerization. Furthermore polycondensation catalysis reactions have to be carried out on a scale of at least 10 g to 1000 g, commonly about 100 g to 500 g. Also, results obtained using conventional screening methods are not predictable for catalyst activities on a large, i.e. industrial scale.

The above problems are particularly pertinent when a large amount of catalysts have to be screened, especially when only a small amount of starting material, e.g. less than 10 g, is available.

It is an object of the present invention to avoid the above problems and to provide a more efficient method for screening polycondensation catalysts.

It is a further object of the present invention to provide a new method for screening of polycondensation catalysts, that can also be used for small amounts of sample.

SUMMARY OF THE INVENTION

The above objects are achieved according to the present invention by a method for screening of polycondensation catalysts, wherein at least two polycondensation catalysis reactions are performed simultaneously under substantially equivalent conditions in at least two reaction cells, using a sample comprising material to be polycondensated and a catalyst to be screened, and wherein the performances of the catalysts are analyzed, wherein:
  the polycondensation reactions are performed in the at least two reaction cells which are present in one reaction room;
  the reaction room is heated such that the reaction cells in the reaction room have, at least temporarily a substantially equivalent temperature of a value >150° C.;
  the reaction room is depressurized such that in the reaction room, at least temporarily, a reduced pressure <100 mbar is maintained; and
  in each separate reaction cell a pre-selected amount of sample is used in the form of a film on a surface of the reaction cell such that a ratio of sample weight to reaction cell surface area covered with said film of less than 1 $g/cm^2$ is obtained.

Herewith the screening of catalytic activity of polycondensation catalysts can be performed in a surprisingly simple and efficient way. Also, the results of the screening of the method of the present invention are well reproducible, in contrast to conventional screening methods. The method of the present invention enables the simultaneous polymerization of 2 to even more than 1000 samples under substantially the same conditions. As the catalytic activities of the different catalysts are obtained under substantially the same conditions, the method of the present invention provides for the possibility of discrimination of different catalysts.

Furthermore, the amount of sample required for each polymerization can be reduced to less than 10 g, to as low as less than 100 mg.

According to the present invention the screening process can thus be speeded up significantly and can be performed on a small scale. These results obtained according to the present invention on a small scale also predict, in contrast to conventional catalyst screening methods, the results to be obtained on a larger scale, i.e. in performing polycondensation reactions on an industrial scale, as the catalysts are used in the form of a film in both the method of the present invention and the industrial scale polycondensation reactions.

Also, no stirring of the reaction samples to promote volatilization of water and polycondensation byproducts such as water, alcohol or glycols in order to increase molecular weight is required, as the results of the screening method of the present invention provides relative reactivities that can be correlated to known polymerization experiments. To this end one or more catalysts with known reactivity can be included in each set of polymerizations to serve as a control or reference.

Further, variation of reaction conditions can be minimized for each set of experiments that are conducted simultaneously. In the method according to the present invention the reaction room is heated such that the reaction cells in the reaction room have, at least temporarily i.e. at least during the polycondensation reaction, a substantially equivalent temperature of a value>150° C. The person skilled in the art will readily understand that the temperature may be changed on purpose in all the reaction cells at the same time, e.g. using a temperature program. Also, the reaction room may be heated such that, when the reaction room comprises different sets of reaction cells, the temperature in the different reaction cells of one set is substantially the same, while the temperature between different sets may differ.

In the method according to the present invention first a sample preparation takes place. Material to be polycondensated, such as a low molecular weight polyester oligomer, is doped with a certain amount of catalyst. This can for instance be accomplished by taking a quantity of oligomer, adding catalyst, melting and stirring the mixture to obtain a homogeneous "masterbatch" melt or dispersion, and then a small portion is loaded in one of the reaction cells. The person skilled in the art will readily understand that any other suitable sample preparation may take place instead. Also a ready-made sample may be used.

Thereafter, polycondensation reactions are performed simultaneously in at least two reaction cells which are present in one and the same reaction room under substantially the same conditions of temperature, pressure, etc. as outlined above. The reaction cells are heated simultaneously to the desired reaction temperature and under the desired vacuum. If desired, the reactions may also be conducted under a stream of inert dry gas or under a stream of dry air.

An important aspect of the present invention is that only a small amount of sample is used in each reaction cell and that the ratio of sample weight to reaction cell surface area covered with the sample is kept low, as a film of sample is used. It has been found that herewith diffusion of polycondensation byproducts, such as water, can be promoted resulting in an efficient polycondensation reaction.

After the polymerization reactions the performances of the catalysts are analyzed. Analysis of the performances may for example be performed by determining the extent of reaction. To this end IV (intrinsic viscosity), GPC (gel permeation chromatography) and NMR (nuclear magnetic resonance) measurements may, and preferably will, be conducted, for example. Of course, also other analytical methods may be used such as IR (infrared spectroscopy), color, DSC (differential scanning calorimetry), etc.

According to the present invention it is preferred that the reaction room is heated such that the reaction cells in the reaction room have a substantially equivalent temperature of a value between 200-320° C., preferably 230-300° C.

It has been found that herewith good polycondensation reaction results can be obtained without desintegration of the obtained products. Further, the results obtained in the different reaction cells can be suitable compared, as the conditions of p, T, . . . are substantially the same.

Further it is preferred according to the present invention that the reaction cells are arranged such that the temperature in each of the at least two reaction cells is maintained substantially equivalent.

It has been found that the temperature gradient in the reaction room may be substantial when the reaction cells are arranged in a random orientation, even when a heat transfer medium such as an oil bath is used in the reaction room.

Preferably the reaction room is depressurized such that, at least temporarily, a reduced pressure below 10 mbar is maintained, more preferably below 5 mbar, most preferably a value between 0.01-2 mbar. Herewith diffusion of the byproducts will be such, that cross-contamination between the different reaction cells is significantly minimized. Also, the level of cross-contamination between the reaction cells will be equal for all cells. A pressure value between 0.01-2 mbar is often required at the end of the polycondensation reaction as a driving force for the reaction.

Further, the polycondensation reactions are preferably performed such that in each separate reaction cell a ratio of sample weight to reaction cell surface area covered with said film of less than 0.5 g/cm$^2$ is obtained, preferably of less than 0.2 g/cm$^2$.

Herewith diffusion of polycondensation byproducts, such as water, can be promoted even further, resulting in an efficient polycondensation reaction Advantageously, in each separate reaction cell a pre-selected amount of less than 2 g sample, preferably less than 1 g, more preferably between 100 mg and 1 mg sample is used.

In a further aspect the present invention relates to an apparatus suitable for performing the method of the present invention, the apparatus comprising:
  a sealable reaction room containing at least two reaction cells;
  vacuum means for providing a reduced pressure of <100 mbar in the reaction room;
  heating means for providing a substantially constant temperature of >150° C. in the reaction cells, wherein the at least two reaction cells are arranged such that a substantially equivalent temperature in substantially all reaction cells can be maintained.

Herewith the screening of catalytic activity of polycondensation catalysts can be performed in a surprisingly simple and efficient way. The apparatus of the present invention enables the simultaneous polymerization of at least 2 to even more than 1000 samples under substantially the same conditions. Preferably at least 5 samples, more preferably at least 10 samples are polymerized simultaneously. Furthermore, the amount of sample required for each polymerization can be reduced to less than 10 g, to as low as less than 100 mg.

Using the apparatus according to the present invention the screening process can be performed in a very efficient and surprisingly simple way. Also small amounts of starting material can be used. Further, variation of reaction conditions between different reaction cells can be minimized for each set of experiments that are conducted simultaneously.

The reaction room containing or holding the at least two, preferably more than five reaction cells may e.g. be a self-contained block of metal, ceramic or glass with individual cells formed within the block. Instead the reaction room may be a holder that provides spaces for individual, removable cells (such as vials). Preferably, removable cells are used, as they can be easily transported and weighted separately. As an example the reaction room may be a flat-bottomed kettle with a gasket-sealed top which is connected to a vacuum pump.

As heating means preferably a heat transfer fluid bath (such as an oil bath) or a high conductivity metal block is used. Of course, any other suitable liquid or solid heating means, such as silicone oils, molten metal salt, sand, metal shavings and the like, may be used as long as it is stable under reaction conditions.

It has been found that the temperature gradient in the reaction room may still be substantial when the reaction cells are arranged in a random orientation, even when a heat transfer medium such as an oil bath is used in the reaction room.

To minimize this problem the reaction cells are, in one embodiment of the present invention, arranged in a row. It has been found that the outermost reaction cells indeed may suffer from a temperature gradient, and therefore the reactions performed therein may not be under the substantially same conditions. However, the other reaction cells in the row do have the same temperature. These other reaction cells may therefore suitably be used for comparing polycondensation catalysts. The same applies for reaction cells arranged in two rows or two sets of two rows which two sets are spaced with a suitable distance such that a substantially equivalent temperature in substantially all reaction cells (apart from the outermost reaction cells in each rows) can be maintained. In this respect it is noted that, of course, the polycondensation reactions performed in the different reaction cells may provide for small temperature gradients because of the different reactions in the different reaction cells. The same applies for diffusion rates.

According to an other, even more preferred embodiment of the apparatus according to the present invention, the reaction cells are placed in a circular arrangement within the reaction room.

Herewith, in all reaction cells in the circular arrangement, a substantially equivalent temperature can be maintained.

More polycondensation reactions may be performed at the same time, while maintaining a substantially equivalent temperature, when the reaction cells are arranged in two concentric circles.

In order to provide a more even heat distribution when using two concentric circles, a well or projection may be used such that the reaction cells are placed around the projection.

An important aspect of the apparatus of the present invention is therefore that the local temperature environment of each reaction cell can be made substantially the same, such that screening of polycondensation catalyst can be suitably performed. Also, the special arrangement of the reaction cells according to the present invention ensures that cross-contamination due to differences in local temperature and/or diffusion environments in the different reaction cells is significantly minimized. Further, the level of cross-contamination, if any, between the reaction cells will be substantially equal for all cells.

According to a preferred embodiment of the apparatus according to the present invention, the at least two reaction cells are held in a rack.

Herewith the reaction cells can be easily placed in the reaction room and, after polymerization of the samples contained therein, transferred to an analyzing instrument.

The person skilled in the art will readily understand that the apparatus according to the present invention may also be used for other uses than screening polycondensation catalysts, wherein local temperatures in at least two different reaction cells have to be substantially the same.

In an even further aspect the present invention relates to the use of the apparatus according to the present invention in screening of polycondensation catalysts.

BRIEF DESCRIPTION OF THE DRAWINGS

Hereinafter the present invention will be illustrated in more detail by a drawing. Herein shows:

FIG. 1 a schematic cross-sectional side view of the apparatus according to the present invention;

FIG. 2 a schematic top view of the arrangement of the reaction cells in the apparatus of FIG. 1;

FIG. 3 a schematic cross-sectional side view of a further embodiment of the apparatus according to the present invention; and FIG. 4 a schematic top view of the arrangement of the reaction cells in the apparatus of FIG. 3.

DETAILED DESCRIPTION OF THE INVENTION

FIG. 1 shows a schematic cross-sectional side view of the apparatus 1 according to the present invention. The apparatus 1 comprises a flat-bottomed kettle 2 (e.g. having an internal diameter of 135 mm), which kettle 2 is sealable with a gasket top 3. In the shown embodiment, eight reaction cells 4 (e.g. vials having diameter×height of 25×60 mm) are present inside the kettle 2 (the 'reaction room'), placed in a module or rack 5. The kettle 2 is connected at 6 with a vacuum pump (not shown). The apparatus 1 is further provided with a heat transfer medium 7, such as sand, oil, or a massive metal block (preferably comprising aluminum or copper), to be heated during use, e.g. by an external oil bath (not shown). When a massive metal block is used, preferably a tight connection between the reaction cells and the metal block is used. In use of the apparatus 1 a substantially equivalent temperature in substantially all reaction cells can be maintained.

FIG. 2 shows a schematic top view of the arrangement of the eight reaction cells 4 in the apparatus 1 of FIG. 1.

FIG. 3 shows a schematic cross-sectional side view of a further embodiment of the apparatus 1 according to the present invention. The apparatus 1 comprises a flat-bottomed kettle 2 sealable with a gasket top 3. In the shown embodiment, thirty-two reaction cells 4 are present inside the kettle 2, placed in a module or rack 5. In the center of the bottom of the kettle 2 a well or projection 8 is present around which the reaction cells are placed in a circular arrangement. The kettle 2 is placed in an oil bath 9. Using the apparatus 1, the local temperature environment of each reaction cell 4 can be maintained substantially the same.

Finally, FIG. 4 shows a schematic top view of the arrangement of the thirty-two reaction cells 4 in the apparatus 1 of FIG. 3.

Hereinafter the method of the present invention will be illustrated in more detail by Examples.

Example 1

Preparation of Oligomer Samples

A 50 ml 3-neck flask with magnetic stir bar was charged with 14 g PTT (poly(trimethylene terephtalate) oligomer and 7.3 mg Ti(OBu)$_4$. In a fume hood the reaction flask was connected to nitrogen and vacuum via a Firestone valve, degassed with nitrogen, and heated in a 240° C. oil bath. After the oligomer had melted, the reaction mixture was stirred at 240° C. for about 30 minutes, cooled to room temperature and broken up. In several preparations of this type, the amount of oligomer was increased to about 40 g and the appropriate amount of the desired catalyst was added by weight or by micropipette.

Example 2

Polymerization

An apparatus as described in FIG. 1 was used to polymerize the oligomer as prepared in Example 1, the kettle and the reaction cells having the dimensions given between brackets. Sand was used as the heat transfer medium.

Seven of the reaction cells (the center position was not used), being placed in a rack, were charged with about 0.5 g (corresponding to about 0.10 g/cm$^2$) each of oligomer/catalyst mixtures as shown in Table 1. The amount of catalyst (as ppm of metal based on weight of oligomer) is also listed in Table 1. The rack was placed in the kettle and the kettle was sealed.

The kettle was placed in an oil bath and heated to 260° C., while the internal pressure was maintained under 200 mbar pressure and with a slight nitrogen sweep through the flask. When the oil bath reached 260° C., a vacuum of about 1 mbar was applied. After 3 hours the reactor was removed from the oil bath, filled with nitrogen and cooled.

Between 0.31 and 0.43 g product was recovered from each reaction cell and submitted for proton NMR for cyclic dimer and IV in hexafluoroisopropanol. The results are shown in Table 1. As can be seen from Table 1, the relative reactivities are Ti>Sn>Ge, based on either IV or cyclic dimer.

| Catalyst | Amount (ppm) | IV | Cyclic dimer (wt. %) |
| --- | --- | --- | --- |
| Ti (OBu)$_4$ | 73 | 0.44 | 2.1 |
|  | 73 | 0.44 | 2.1 |
|  | 73 | 0.44 | 2.1 |
| Sn (Bu)$_2$O | 72 | 0.32 | 1.5 |
|  | 72 | 0.32 | 1.5 |
| Ge (OEt)$_4$ | 76 | 0.19 | 0.5 |
|  | 76 | 0.22 | 0.6 |

For comparison, polymerization reactions were also performed using classical equipment. The same relative reactivities were obtained. However, the total experimental time for one polymerization, including setup and work up, took at least six hours. Furthermore, the polymerization reactions were performed using more than 100 g oligomer per reaction.

Example 3

Minimizing Temperature Differences Between Reaction Cells

It has been found that, even when using a heat transfer medium in a kettle as described in FIG. 1, the temperature differences between different reaction cells may even be further minimized. To this end a special arrangement of reaction cells is proposed according to the present invention, e.g. as shown in FIG. 3 and FIG. 4.

The person skilled in the art will understand that many modifications may be made.

The invention claimed is:

1. Method for screening of polycondensation catalysts, wherein at least two polycondensation catalysis reactions are performed simultaneously under substantially equivalent conditions in at least two reaction cells, using a sample comprising material to be polycondensated and a catalyst to be screened, and wherein the performances of the catalysts are analyzed, wherein
   the samples are made by adding the catalyst to be screened to the material to be polycondensated;
   the polycondensation reactions are performed in the at least two reaction cells which are present in one and the same reaction room in the form of a flat-bottomed kettle with a gasket-sealed top which is connected to a vacuum pump, wherein the one reaction room is equipped with a heat transfer medium as heating means;
   the reaction room is heated such that the reaction cells in the reaction room have, at least temporarily, a substantially equivalent temperature of a value >150° C.;
   the reaction room is depressurized such that in the reaction room, at least temporarily, a reduced pressure <100 mbar is maintained; and
   in each separate reaction cell a pre-selected amount of sample is used in the form of a film on a surface of the reaction cell such that a ratio of sample weight to reaction cell surface area covered with said film of less than 1 g/cm$^2$ is obtained and after the polycondensation reactions have been performed the separate samples are analyzed.

2. Method according to claim 1, wherein the reaction room is heated such that the reaction cells in the reaction room have a substantially equivalent temperature of a value between 200-320° C., preferably 230-300° C.

3. Method according to claim 1, wherein the reaction cells are arranged such that the temperature in each of the at least two reaction cells is maintained substantially equivalent.

4. Method according to claim 1, wherein the reaction room is depressurized such that, at least temporarily, a reduced pressure below 10 mbar is maintained, more preferably below 5 mbar, most preferably a value between 0.01-2 mbar.

5. Method according to claim 1, wherein the polycondensation reactions are performed such that in each separate reaction cell a ratio of sample weight to reaction cell surface area covered with said film of less than 0.5 g/cm$^2$ is obtained, preferably of less than 0.2 g/cm$^2$.

6. Method according to claim 1, wherein in each separate reaction cell a pre-selected amount of less than 2 g sample, preferably less than 1 g, more preferably between 100 mg and 1 mg sample is used.

7. Apparatus suitable for performing a method for screening of polycondensation catalysts, wherein at least two polycondensation catalysis reactions are performed simultaneously under substantially equivalent conditions in at least two reaction cells which are present in one and the same sealable reaction room, using a sample comprising material to be polycondensated and a catalysts to be screened, and wherein the performances of the catalysts are analyzed,
   the apparatus comprising:
   said sealable reaction room in the form of a flat-bottomed kettle with a gasket-sealed top containing at least two reaction cells for holding a sample comprising of material to be polycondensated and an added catalyst to be screened;
   vacuum means in the form of a vacuum pump connected to said sealable reaction room for providing a reduced pressure of <100 mbar in the reaction room;
   heating means in the form of a heat transfer medium for providing a substantially equivalent temperature of >150° C. in the reaction cells,
   wherein the at least two reaction cells are arranged such that a substantially equivalent temperature in substantially all reaction cells can be maintained.

8. Apparatus according to claim 7, wherein the reaction cells are arranged in a row.

9. Apparatus according to claim 8, wherein the reaction cells are arranged in two rows.

10. Apparatus according to claim 9, wherein the reaction cells are arranged in two sets of two rows which two sets are spaced with a suitable distance such that a substantially equivalent temperature in substantially all reaction cells can be maintained.

11. Apparatus according to claim 7, wherein the reaction cells are placed in circular arrangement within the reaction room.

12. Apparatus according to claim 11, wherein the reaction cells are arranged in two concentric circles.

13. Apparatus according to claim 11, wherein the reaction cells are placed around a projection.

14. Apparatus according to claim 7, wherein the at least two reaction cells are held in a rack.

15. Use of the apparatus according to claim 7 in screening of polycondensation catalysts, wherein at least two polycondensation catalysis reactions are performed simultaneously under substantially equivalent conditions in at least two reaction cells wherein the at least two reaction cells are in the form of vials, using a sample comprising material to be polycondensated and a catalysts to be screened, and wherein the performances of the catalysts are analyzed, wherein
   the polycondensation reactions are performed in the at least two reaction cells which are present in one reaction room, wherein the one reaction room is equipped with a heating means;
   the reaction room is heated such that the reaction cells in the reaction room have, at least temporarily, a substantially equivalent temperature of a value >150° C.;
   the reaction room is depressurized such that in the reaction room, at least temporarily, a reduced pressure <100 mbar is maintained; and
   in each separate reaction cell a pre-selected amount of sample is used in the form of a film on a surface of the reaction cell such that a ratio of sample weight to reaction cell surface area covered with said film of less than 1 g/cm² is obtained wherein after polycondensation reactions have been performed the separate samples are analyzed.

16. Method for screening of polycondensation catalysts, wherein at least two polycondensation catalysis reactions are performed simultaneously under substantially equivalent conditions in at least two reaction cells wherein the at least two reaction cells are in the form of vials, using a homogeneous sample comprising material to be polycondensated and a catalyst to be screened, and wherein the performances of the catalysts are analyzed, wherein the samples are made by adding the catalyst to be screened to the material to be polycondensated, and stirring the mixture to obtain a homogeneous sample;

the polycondensation reactions are performed in the at least two reaction cells which are present in one reaction room, wherein the one reaction room is equipped with a heating means;

the reaction room is heated such that the reaction cells in the reaction room have, at least temporarily, a substantially equivalent temperature of a value >150° C.;

the reaction room is depressurized such that in the reaction room, at least temporarily, a reduced pressure <100 mbar is maintained; and in each separate reaction cell a pre-selected amount of sample is used in the form of a film on a surface of the reaction cell such that a ratio of sample weight to reaction cell surface area covered with said film of less than 1 g/cm² is obtained and after the polycondensation reactions have been performed the separate samples are analyzed.

* * * * *